US011972564B2

(12) United States Patent
Brandenburg et al.

(10) Patent No.: US 11,972,564 B2
(45) Date of Patent: Apr. 30, 2024

(54) RECORDING MEDIUM, INFORMATION PROCESSING DEVICE, INFORMATION PROCESSING METHOD, TRAINED MODEL GENERATION METHOD, AND CORRELATION IMAGE OUTPUT DEVICE

(71) Applicant: Splink, Inc., Tokyo (JP)

(72) Inventors: Felix Julian Brandenburg, Tokyo (JP); Akihiro Okuno, Tokyo (JP); Yuki Aoyama, Tokyo (JP)

(73) Assignee: Splink, Inc., Tokyo (JP)

(*) Notice: Subject to any disclaimer, the term of this patent is extended or adjusted under 35 U.S.C. 154(b) by 0 days.

(21) Appl. No.: 18/020,834

(22) PCT Filed: Aug. 14, 2020

(86) PCT No.: PCT/JP2020/030905
§ 371 (c)(1),
(2) Date: Feb. 10, 2023

(87) PCT Pub. No.: WO2022/034691
PCT Pub. Date: Feb. 17, 2022

(65) Prior Publication Data
US 2023/0230233 A1   Jul. 20, 2023

(51) Int. Cl.
*G06T 7/00* (2017.01)
*G06V 10/25* (2022.01)
(Continued)

(52) U.S. Cl.
CPC .......... *G06T 7/0012* (2013.01); *G06V 10/25* (2022.01); *G16H 30/20* (2018.01); *G16H 50/20* (2018.01);
(Continued)

(58) Field of Classification Search
CPC ......... G06T 7/0012; G06T 2207/10088; G06T 2207/30016; G16H 30/20; G16H 50/20; G06V 10/25
See application file for complete search history.

(56) References Cited

U.S. PATENT DOCUMENTS

2014/0233825 A1   8/2014   Yoneda
2015/0235358 A1   8/2015   Momose et al.
(Continued)

FOREIGN PATENT DOCUMENTS

JP   2020-503991 A   2/2020
WO   WO2013047583 A1   4/2013
(Continued)

OTHER PUBLICATIONS

Van et al. ("Simultaneous quantitative susceptibility mapping and Flutemetamol-PET suggests local correlation of iron and β-amyloid as an indicator of cognitive performance at high age"). (Year: 2018).*
(Continued)

*Primary Examiner* — Vu Le
*Assistant Examiner* — Winta Gebreslassie
(74) *Attorney, Agent, or Firm* — Bret E. Field; Bozicevic, Field & Francis LLP

(57) ABSTRACT

To provide a recording medium capable of estimating the early signs of diseases relating to amyloid β without using a PET image, an information processing device, an information processing method, a trained model generation method, and a correlation image output device.
The recording medium recording the computer program causes a computer to execute processes of: acquiring an MRI image of a subject; and inputting the acquired MRI image to a trained model that outputs a correlation image representing a correlation between a magnetic susceptibility
(Continued)

capable of being specified on the basis of the MRI image and amyloid β in a case where the MRI image is input, and outputting the correlation image representing the correlation between the magnetic susceptibility of the subject and amyloid β.

10 Claims, 14 Drawing Sheets

(51) Int. Cl.
    *G16H 30/20*     (2018.01)
    *G16H 50/20*     (2018.01)
(52) U.S. Cl.
    CPC ............... *G06T 2207/10088* (2013.01); *G06T 2207/30016* (2013.01)

(56) References Cited

U.S. PATENT DOCUMENTS

| | | | |
|---|---|---|---|
| 2018/0268942 | A1 | 9/2018 | Kamali-Zare et al. |
| 2018/0310869 | A1* | 11/2018 | Yablonskiy ........ A61B 5/14542 |

FOREIGN PATENT DOCUMENTS

| | | | |
|---|---|---|---|
| WO | WO2014034724 | A1 | 3/2014 |
| WO | WO2018064715 | A1 | 4/2018 |
| WO | WO-2018176082 | A1 * | 10/2018 |

OTHER PUBLICATIONS

Kudo, MRI Diagnosis of Alzheimer's Disease Using QSM, Nuclear medicine technology, Oct. 2018, vol. 38, pp. 395; English abstract enclosed.

English Translation of International Search Report for PCT Application No. PCT/JP2020/030905 dated Sep. 29, 2020, 2 pages.

Ayton et al., Cerebral quantitative susceptibility mapping predicts amyloid-β-related cognitive decline, BRAIN, 140; (8):2112-2119, 2017.

Chen et al., QSMGAN: Improved Quantitative Susceptibility Mapping using 3D Generative Adversarial Networks with Increased receptive field, NeuroImage, 207:1-26, Feb. 15, 2020.

Lan et al., SC-GAN: 3D self-attention conditional GAN with spectral normalization for multi-modal neuroimaging synthesis, bioRxiv, Jun. 11, 2020.

Office Action for Japanese Application No. 2022-542567 dated Aug. 8, 2023, with its English Translation, 9 pages.

Kudo et al., IC-P-139, A Multicenter Study of the Correlation between the Quantitative Susceptibility Mapping of Magnetic Resonance Imaging and Amyloid Positron Emission Tomography, Alzheimer's Association International Conference 2019, Poster Presentation, Jul. 13, 2019, vol. 15, Issue 7S Part 2, p. 114-p. 115.

Kudo, A new world of diagnosis expands with QSM Analysis, innnavi net, vol. 37, 2019, with its machine translation, 11 pages.

Office Action for Japanese Application No. 2022-542567 dated Dec. 12, 2023, with its machine translation, 7 pages.

* cited by examiner

F I G. 1
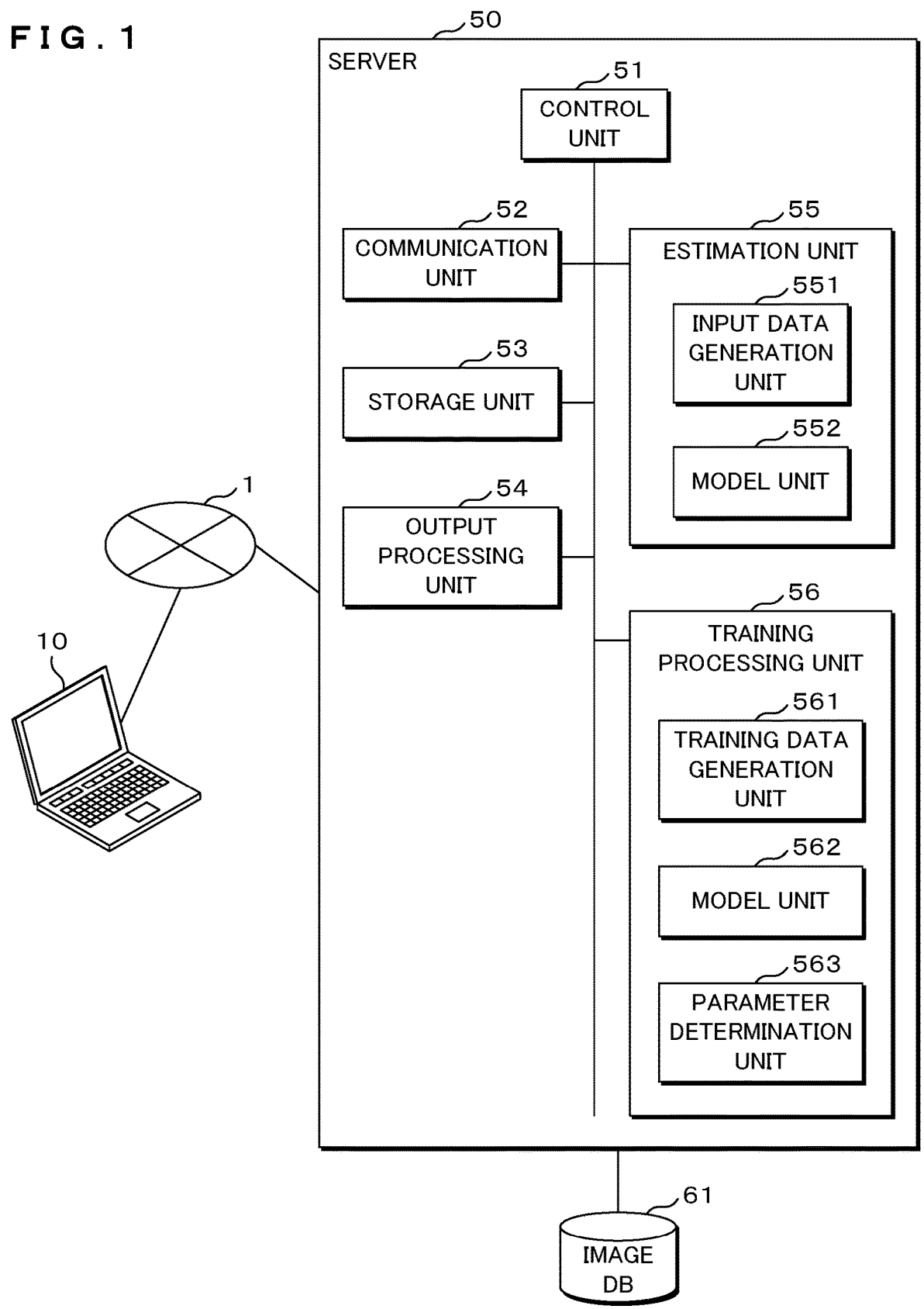

FIG. 5
| | CORRELATION IMAGE | CORRELATION IMAGE + MRI IMAGE |
|---|---|---|
| CLUSTER | 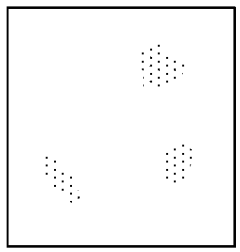 | 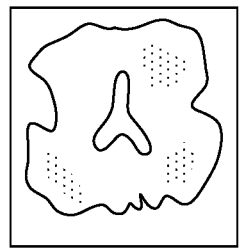 |
| VOXEL | 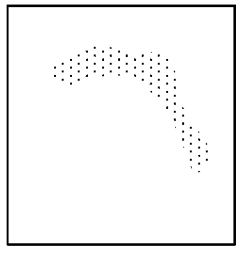 | 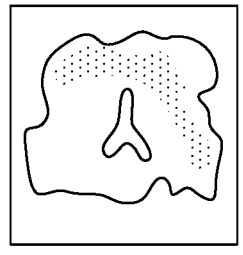 |
| REGION OF INTEREST | 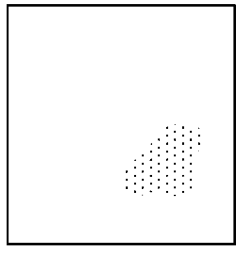 | 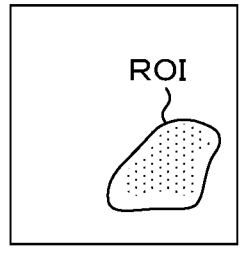 |

FIG. 7
| CURRENT | AFTER ONE YEAR | AFTER TWO YEARS |
|---|---|---|
| 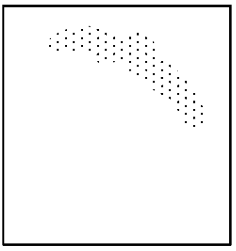 | 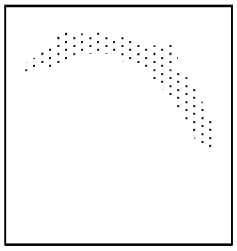 | 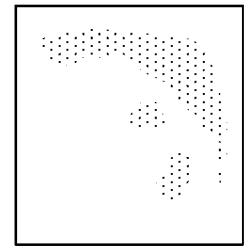 |

F I G . 13
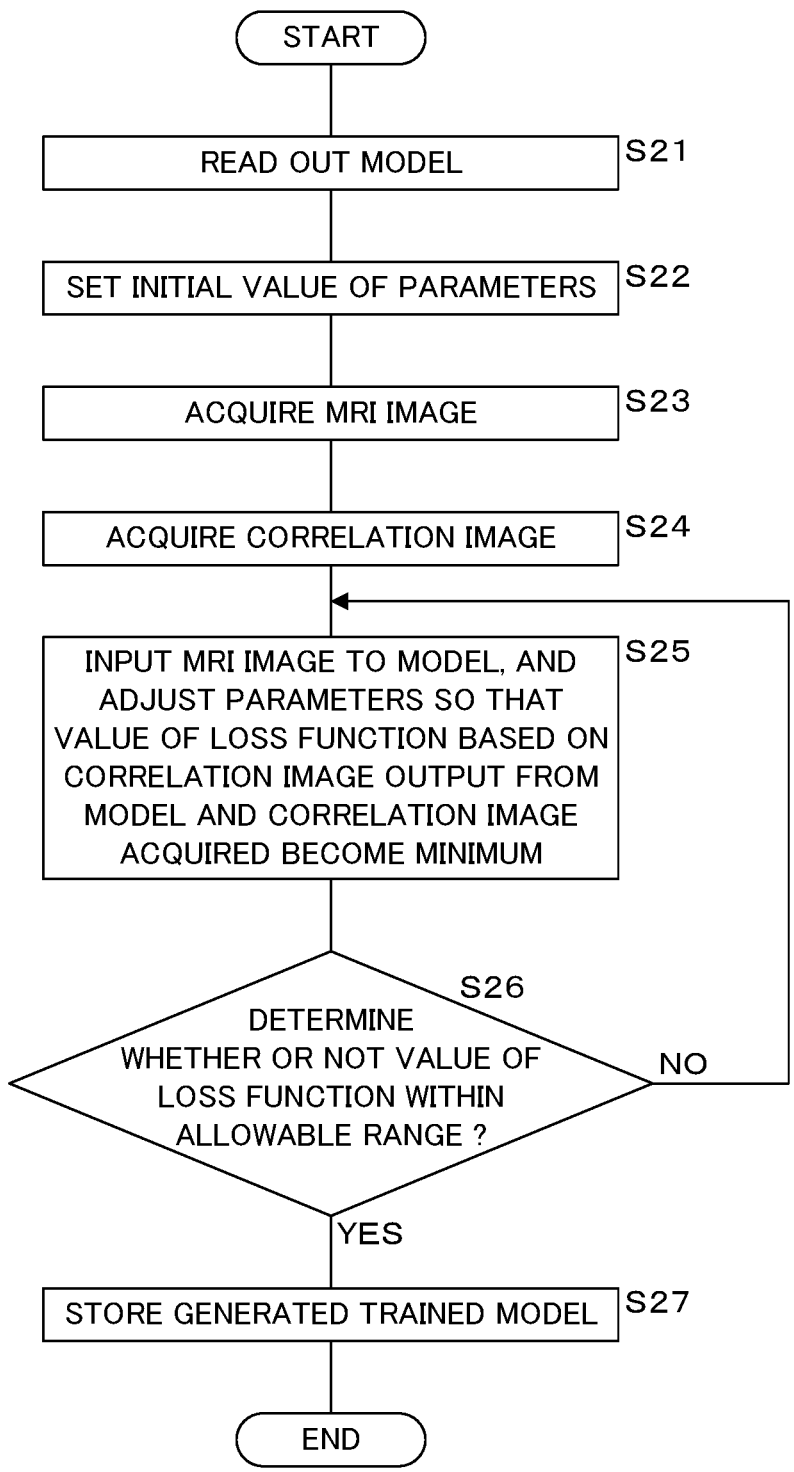

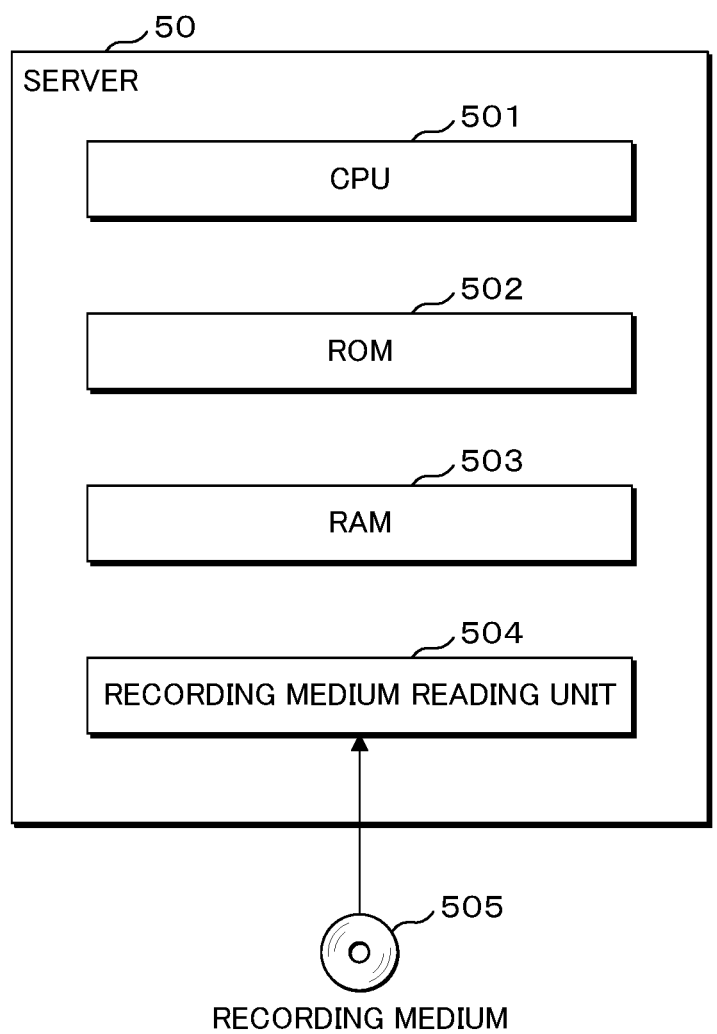
F I G . 14

RECORDING MEDIUM, INFORMATION PROCESSING DEVICE, INFORMATION PROCESSING METHOD, TRAINED MODEL GENERATION METHOD, AND CORRELATION IMAGE OUTPUT DEVICE

CROSS-REFERENCE TO RELATED APPLICATIONS

This application is the national phase under 35 U.S.C. § 371 of PCT International Application No. PCT/JP2020/030905 which has an International filing date of Aug. 14, 2020 and designated the United States of America.

FIELD

The present disclosure relates to a recording medium, an information processing device, an information processing method, a trained model generation method, and a correlation image output device.

BACKGROUND

In recent, as the population ages, the number of dementia patients and dementia reserves (mild cognitive impairment) is increasing. The main disease that causes the dementia is called Alzheimer's disease. Although the cause of the Alzheimer's disease has not yet been elucidated, a peculiar lesion is observed in the brain as the disease progresses. For example, deposition of senile plaques by amyloid $\beta$ is known on an outer side of nerve cells. It has been known that deposition of senile plaques occurs from the earliest stage of development of the Alzheimer's disease, and begins well before clinical symptoms appear (for example, over a decade ago).

International Publication No. WO 2014/034724 discloses an apparatus that injects and administers a drug to be bound to amyloid $\beta$ in a brain tissue to a subject, and uses a positron emission tomography (PET) image that represents a concentration distribution of the drug on a cut surface that transverses the brain.

SUMMARY

However, in photographing the PET image by using the drug, even though a small amount is used, there is a concern that a radioactive substance is required to be ingested into the body, and a patient will be exposed to radiation.

In addition, the drug may not be administered to a patient who is suffering from certain diseases such as kidney diseases.

The disclosure has been made in consideration of such circumstances, and an object thereof is to provide a recording medium capable of estimating the early signs of diseases relating to amyloid $\beta$ without using a PET image, an information processing device, an information processing method, a trained model generation method, and a correlation image output device.

A computer readable non-transitory recording medium recording a computer program according to an embodiment of the disclosure causes a computer to execute processes of: acquiring an MRI image of a subject; and inputting the acquired MRI image to a trained model that outputs a correlation image representing a correlation between a magnetic susceptibility capable of being specified on the basis of the MRI image and amyloid $\beta$ in a case where the MRI image is input, and outputting the correlation image representing the correlation between the magnetic susceptibility of the subject and amyloid $\beta$.

An information processing device according to the embodiment of the disclosure includes: an acquisition unit that acquires an MRI image of a subject; and an output unit that inputs the acquired MRI image to a trained model that outputs a correlation image representing a correlation between a magnetic susceptibility capable of being specified on the basis of the MRI image and amyloid $\beta$ in a case where the MRI image is input, and outputs the correlation image representing the correlation between the magnetic susceptibility of the subject and amyloid $\beta$.

An information processing method according to the embodiment of the disclosure includes: acquiring an MRI image of a subject; and inputting the acquired MRI image to a trained model that outputs a correlation image representing a correlation between a magnetic susceptibility capable of being specified on the basis of the MRI image and amyloid $\beta$ in a case where the MRI image is input, and outputting the correlation image representing the correlation between the magnetic susceptibility of the subject and amyloid $\beta$.

A trained model generation method according to the embodiment of the disclosure includes: acquiring an MRI image; acquiring a correlation image representing a correlation between a magnetic susceptibility and amyloid $\beta$; and generating a trained model that outputs a correlation image representing a correlation between a magnetic susceptibility capable of being specified on the basis of the MRI image, and amyloid $\beta$ by using the acquired MRI image and the correlation image.

A correlation image output device according to the embodiment of the disclosure outputs a correlation image representing a correlation between a magnetic susceptibility of a subject and amyloid $\beta$ in a case where an MRI image of the subject is input.

According to the invention, it is possible to estimate the early signs of dementia without using a PET image.

The above and further objects and features of the invention will more fully be apparent from the following detailed description with accompanying drawings.

BRIEF DESCRIPTION OF THE DRAWINGS

FIG. 1 is a schematic view illustrating an example of a configuration of an information processing system of an embodiment.

FIG. 5 is a schematic view illustrating a first example of a brain state estimation result obtained by the estimation unit.

FIG. 7 is a schematic view illustrating a second example of the brain state estimation result obtained by the estimation unit.

FIG. 13 is a flowchart illustrating an example of a procedure of a trained model generation process.

FIG. 14 is a schematic view illustrating other example of a configuration of an information processing system of an embodiment.

Hereinafter, an embodiment of the disclosure will be described with reference to the accompanying drawings. FIG. 1 is a schematic view illustrating an example of a configuration of an information processing system of this embodiment. The information processing system includes a server 50 as an information processing device. The server 50 is connected to a communication network 1. A terminal device 10 that is used by a medical staff, a researcher, or the like is connected to the communication network 1. As the terminal device 10, for example, a personal computer, a smartphone, a tablet, or the like can be used. In addition, the terminal device 10 can acquire or transmit a medical image from an MRI device (not illustrated) or the like.

Figure 2:
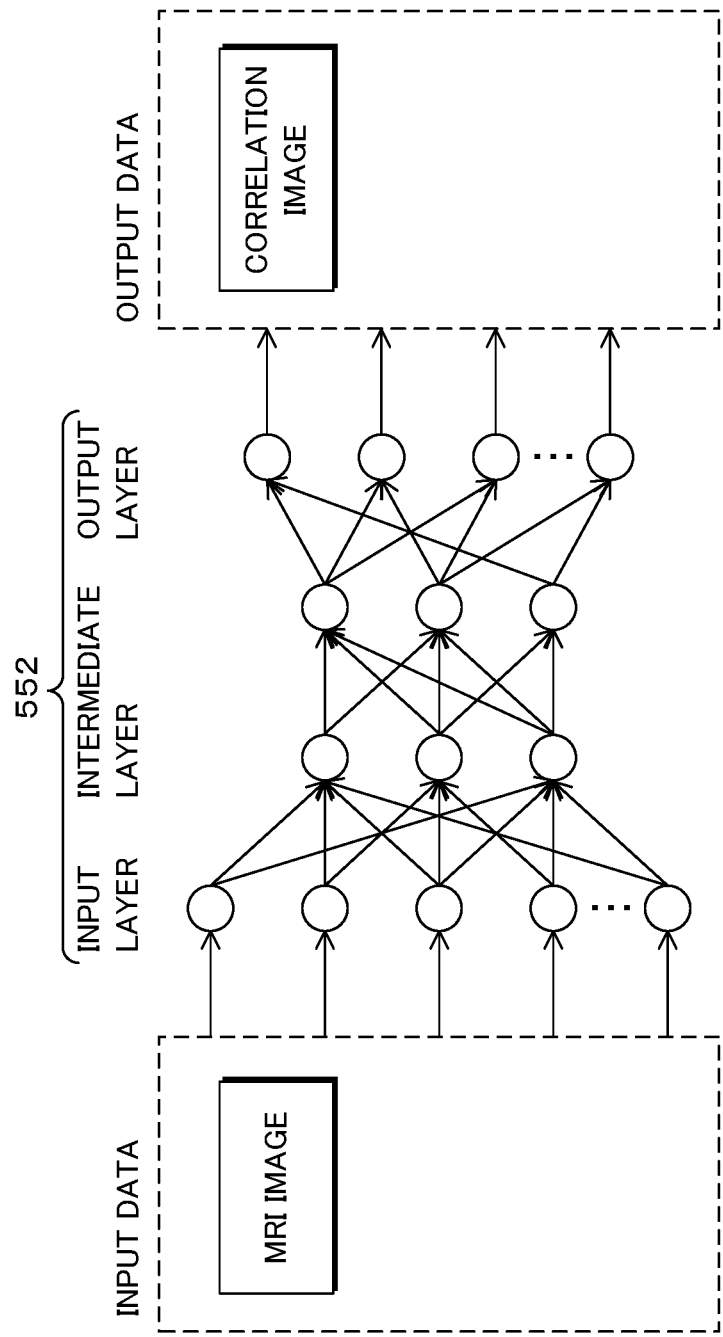
FIG. 2 is a schematic view illustrating a first example of a brain state estimation method by an estimation unit.

The server 50 includes a control unit 51 that controls the entirety of the server 50, a communication unit 52, a storage unit 53, an output processing unit 54, an estimation unit 55, and a training processing unit 56. An image DB 61 is connected to the server 50. The control unit 51 can be constituted by a central processing unit (CPU), a read only memory (ROM), a random access memory (RAM), or the like. Respective functions of the server 50 may be distributed to a plurality of servers. For example, the estimation unit 55 may be provided in the server 50, and the training processing unit 56 may be provided in another server. In addition, the information processing device may be assembled to the server 50, but may be assembled to another device other than the server 50.

The communication unit 52 is constituted by a required communication module or the like, and provides a communication function with the terminal device 10 through the communication network 1. For example, the communication unit 52 can acquire a medical image (for example, an MRI image) of a subject, time information, and the like from the terminal device 10. Details of the MRI image and the time information will be described later. The MRI image is also referred to as MR image.

The storage unit 53 can be constituted by a hard disk, a semiconductor memory, or the like, and can store required data such as data obtained as a result of processing in the server 50.

The output processing unit 54 performs an output process when providing a brain state estimation result to the terminal device 10.

The estimation unit 55 has a function of performing a brain state estimating process, and includes an input data generation unit 551 and a model unit 552. The model unit 552 is constituted by a semiconductor memory, a hard disk, or the like, and stores a model (trained model) that is generated by machine learning. For example, the trained model can be constituted by a neural network. The input data generation unit 551 generates data that is input to a learning model when performs the brain state estimating process.

The training processing unit 56 has a function of generating a trained model by machine learning, and includes a training data generation unit 561, a model unit 562, and a parameter determination unit 563. The model unit 562 is constituted by a semiconductor memory, a hard disk, or the like, and stores a model before machine learning. A trained model that is generated by performing the machine learning by the training processing unit 56 can be stored in the model unit 552 of the estimation unit 55. Note that, a model during the machine learning, a model for retraining, and a trained model can be stored in the model unit 562. In addition, the training processing unit 56 is not an essential configuration, and may be provided in an additional server that performs a training process. The training data generation unit 561 generates input data for training and teaching data when generating the trained model. The parameter determination unit 563 adjusts a parameter (for example, a weight, a bias, and the like) of a neural network when generating a trained model, and finally determines the parameter.

For example, the training processing unit 56 can be constituted by combining hardware such as a CPU (for example, a multiprocessor including a plurality of processor cores, or the like), a graphics processing unit (GPU), a digital signal processor (DSP), and a field-programmable gate array (FPGA).

The image DB 61 can record various images which are used in the machine learning when generating a trained model. In addition, the image DB 61 can record various images relating to a brain state estimation result obtained by the server 50.

Next, details of a brain state estimation method by the server 50 will be described. Specifically, with regard to the brain state, an accumulation state of amyloid β in the brain, that is, a distribution state of amyloid β is estimated. The present inventors have found an estimation method of estimating a distribution state of amyloid β of a subject without stopping to the finding that a significant correlation exists between quantitative susceptibility mapping (QSM) that is a method of quantitative imaging a magnetic susceptibility of a biological tissue and an amyloid PET that detects accumulation of amyloid β by positron emission tomography (PET). Hereinafter, details will be described.

FIG. 2 is a schematic view illustrating a first example of the brain state estimation method by the estimation unit 55. The model unit 552 is a trained model, the model is constituted by a neural network and includes an input layer, an intermediate layer, and an output layer, and parameters (a weight, a bias, and the like) of the neural network are determined by machine learning. The input data generation unit 551 inputs an MRI image acquired from the terminal device 10 through the communication unit 52 to the model unit 552 as input data.

The MRI image includes a T1-weighted image and a T2-weighted image. A complex image composed of a real part and an imaginary part can be generated by performing reconstruction processing to a magnetic resonance (MR) signal. An intensity image is an image representing an absolute value of a real part and an imaginary part of each pixel. A phase image representing a phase between the real part and the imaginary part of each pixel is an image representing a phase difference that occurs due to a magnetic susceptibility difference between biological tissues or other factors. Examples of the intensity image and the phase image include the T1-weighted image, the T2-weighted image, and the like. In addition, the MRI image may include an image that is generated from the MRI image by predetermined image processing. For example, a quantitative susceptibility mapping (QSM) image is also referred to as a quantitative magnetic susceptibility mapping image, and can be generated from the MRI image. The QSM image is mapped by quantitatively obtaining a local magnetic susceptibility from a phase image. The magnetic susceptibility is a physical value that represents the likelihood of magnetic polarization (magnetization) that occurs when a substance reacts with an external magnetic field, and since all substances have a weak diamagnetism, a biological tissue shows a slightly negative magnetic susceptibility, and shows a positive magnetic susceptibility when iron deposition occurs. Note that, a variation of the magnetic susceptibility can occur due to a factor other than the iron deposition, for example, fibrosis, deoxygenation of hemoglobin, or the like. Since the magnetic susceptibility can be quantitatively imaged, the amount or a distribution of the iron deposition in the biological tissue, or a variation thereof with the passage of time can be confirmed. The iron deposition in the brain occurs in a wide range, but when the iron deposition excessively occurs in a specific portion, cognitive impairment is caused to occur. In the QSM, contrast is obtained from two physical properties of a paramagnetic substance (mainly, an iron component) and a diamagnetic substance, and iron deposition in each portion in the brain can be confirmed, and the contrast can be used in diagnosis of Alzheimer's disease or the like. Note that, in generation of the QSM image, a known method may be used.

Note that, in this specification, the MRI image may be an image that can specify a magnetic susceptibility and can be generated from the MRI image. That is, the MRI image also includes the T2-weighted image or a QSM image that is generated from the MRI image by predetermined image processing in addition to the T1-weighted image.

The model unit 552 has a function as a correlation image output device, and can output a correlation image representing a correlation between a magnetic susceptibility and amyloid β in a case where an MRI image relating to the brain is input. In this case, the model unit 552 can also estimate a current distribution state of amyloid β, but the model unit 552 can determine whether to estimate how much future distribution state (for example, after one year, after two years, or the like) of amyloid β as a specific period in advance. In addition, in a case of performing estimation at a plurality of points of time in the future such as after one year and after two years, the model unit 552 for every specific period specified for each of the plurality of points of time in the future may be prepared. Note that, details of the trained model generation method will be described later.

The correlation image specifies a correlation coefficient r between a magnetic susceptibility and a PET signal (for example, a standardized uptake value ratio (SUV) and a standardized uptake value ratio (SUVR)) of a PET image for each corresponding pixel (voxel) of the MRI image and the PET image. Various methods can be used to illustrate (imaging) the correlation coefficient r, and for example, a voxel having a correlation coefficient r that is equal to or more than a threshold value may be illustrated, or the magnitude of the correlation coefficient r may be identifiably imaged like a heat map. The size of the MRI image, the PET image, and the correlation image is the same in each case, and can be set to, for example, 128×128×64 (totally, 1048576 voxels), but there is no limitation to the size. The SUVR can be obtained by dividing the sum of SUV (the degree of accumulation of amyloid β protein) of four portions (prefrontal area, anterior and posterior cingulate cortex, parietal lobe, lateral temporal lobe) of cerebral gray matter by SUV of a specific reference region (for example, cerebellum, or the like). For example, the correlation coefficient r can be set to satisfy a relationship of 0≤r≤1, and as the correlation coefficient r is closer to 1, the correlation is larger.

Figure 3:
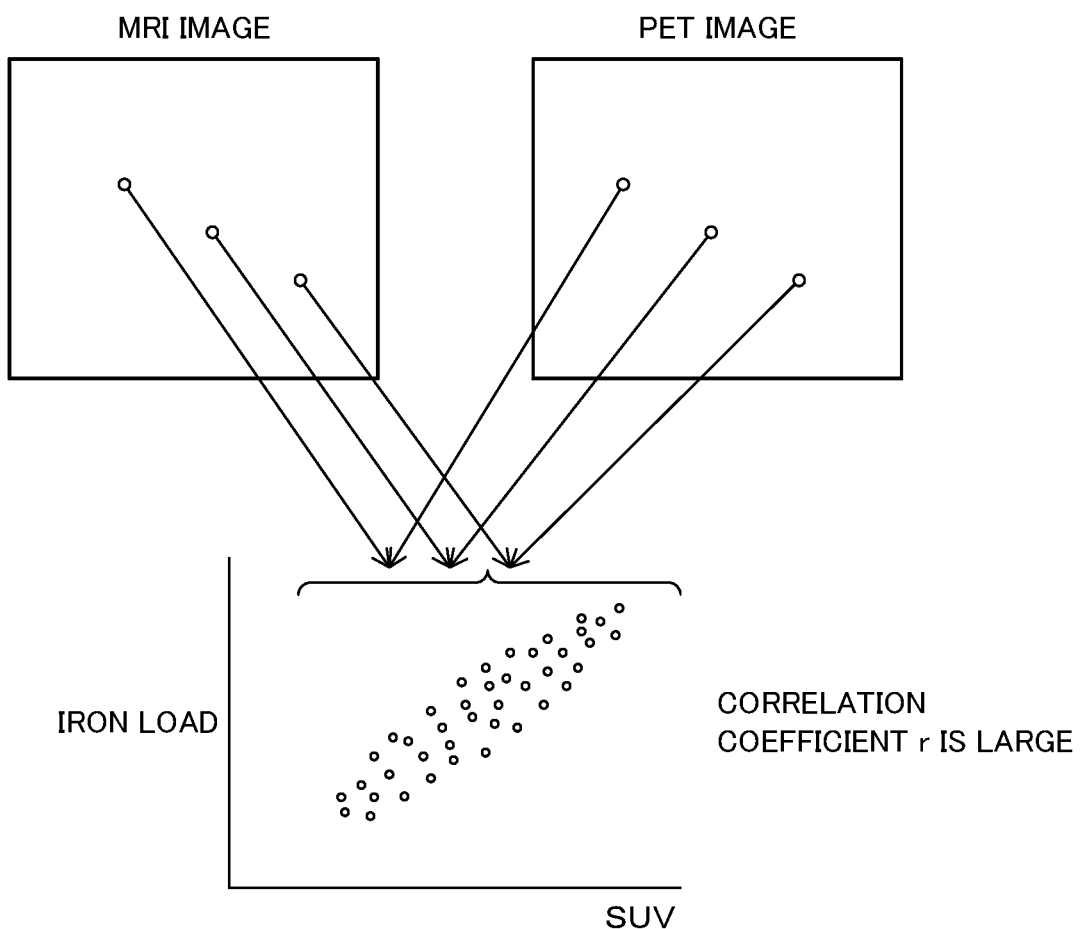
FIG. 3 is a schematic view illustrating an example of a correlation between an MRI image and a PET image in a case where a correlation coefficient is large.

FIG. 3 is a schematic view illustrating an example of a correlation between the MRI image and the PET image in a case where the correlation coefficient r is large. A signal (an iron load, a magnetic susceptibility, or the like in a case of the QSM image) of any voxel of the MRI image and a PET signal of a voxel of the PET image (voxel at the same coordinates on a three-dimensional image) which corresponds to the voxel are mapped to two-dimensional coordinates determined by the signal (iron load) and the PET signal (SUV). For example, in a case where data mapped to the two-dimensional coordinates has a strong relationship between signals as illustrated in FIG. 3, the correlation coefficient r is large. When the number of voxels is equal to or more than a predetermined threshold value, a correlation in a cluster unit can be obtained, and when the number of voxels is less than the predetermined threshold value, a correlation in a voxel unit can be obtained. In addition, a region of interest can be determined in advance, and a correlation in the region of interest unit can be obtained on the basis of voxels in the region of interest.

Figure 4:
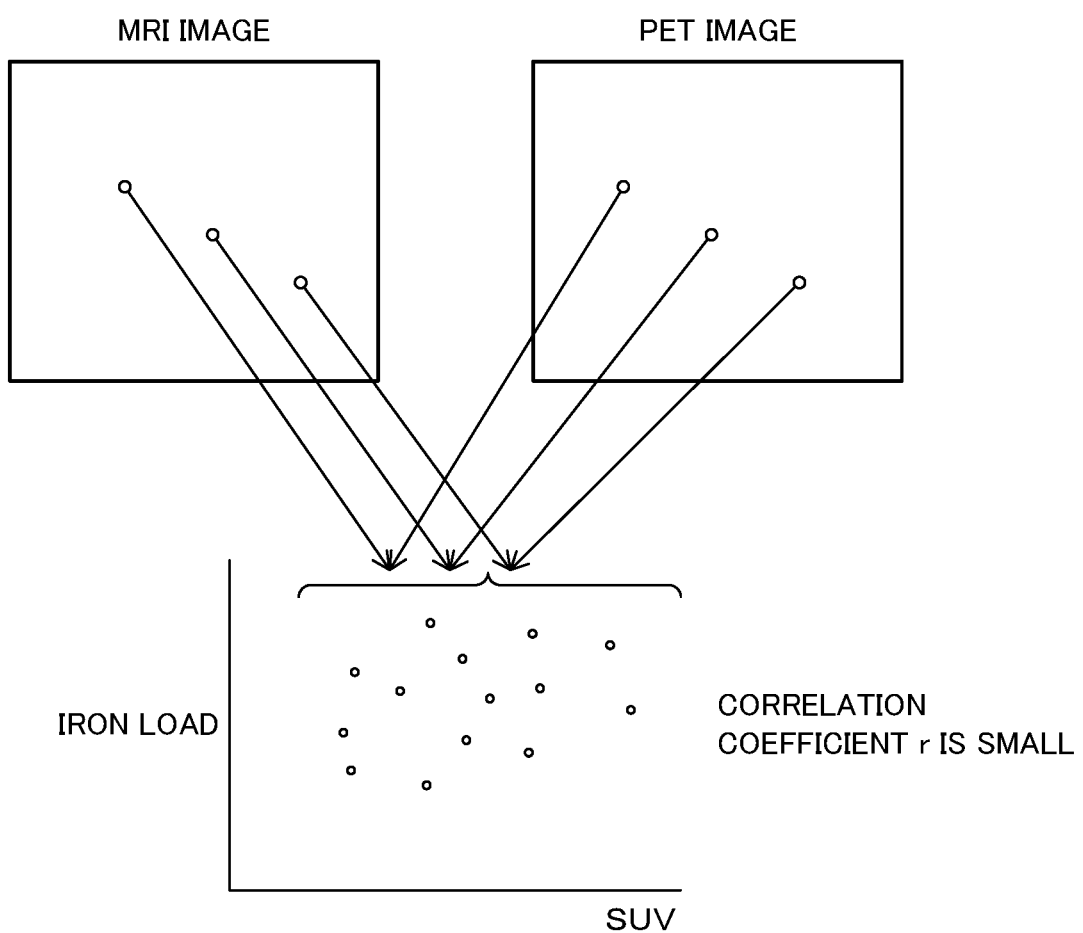
FIG. 4 is a schematic view illustrating an example of the correlation between the MRI image and the PET image in a case where the correlation coefficient is small.

FIG. 4 is a schematic view illustrating an example of the correlation between the MRI image and the PET image in a case where the correlation coefficient r is small. A signal (iron load) of any voxel of the MRI image and a PET signal of a voxel of the PET image (voxel at the same coordinates on a three-dimensional image) which corresponds to the voxel are mapped to two-dimensional coordinates determined by the signal (iron load) and the PET signal (SUV). For example, in a case where data mapped to the two-dimensional coordinates has a strong relationship between signals as illustrated in FIG. 4, the correlation coefficient r is small.

As described above, it is possible to estimate a distribution state of amyloid β in the brain of a subject by inputting an MRI image of the subject to the model unit 552. According to this, it is possible to estimate the early signs of diseases relating to amyloid β without using the PET image. Examples of the disease relating to amyloid β include neurodegenerative diseases such as mild cognitive impairment (MCI), mild cognitive impairment due to Alzheimer disease (MCI due to AD), prodromal Alzheimer disease (prodromal AD), preclinical state of Alzheimer disease/preclinical AD, Parkinson's disease, multiple sclerosis, cognitive decline, cognitive impairment, and amyloid positive/negative diseases.

FIG. 5 is a schematic view illustrating a first example of a brain state estimation result obtained by the estimation unit 55. As described above, the model unit 552 can output a correlation image representing a correlation between a magnetic susceptibility and amyloid β in a case where an MRI image relating to the brain is input. Since the correlation image is an image in which a correlation coefficient between the magnetic susceptibility and amyloid β is specified for every voxel, a value of each voxel shows a value relating to the amount of amyloid β. According to this, when an MRI image of the brain at any point of time is obtained, it is possible to estimate a distribution state of amyloid β in the brain.

In the example of FIG. 5, correlation images are schematically illustrated for every cluster unit, for every voxel unit, and for every region of interest unit. The images illustrated in FIG. 5 can be displayed on the terminal device 10, for example, after being processed by the output processing unit 54. A point in each of the correlation images represents a deposition position of amyloid β. Although not illustrated in the drawing, the value relating to the amount of amyloid β can be shown by a value of a voxel (for example, the degree of contrast).

In addition, the output processing unit 54 can display the correlation image output from the model unit 552 and another MRI image (for example, a T1-weighted image) in an overlapping manner. In the example in FIG. 5, images in which the correlation image and another MRI image overlap each other for every cluster unit, for every voxel unit, and for every region of interest unit are schematically illustrated. As the other MRI image, for example, the T1-weighted image having a characteristic in which a structure of the brain is easy to see can be used. According to this, it is possible to easily determine that the distribution state of amyloid β which is represented by the correlation image corresponds to which portion of the brain.

Figure 6:
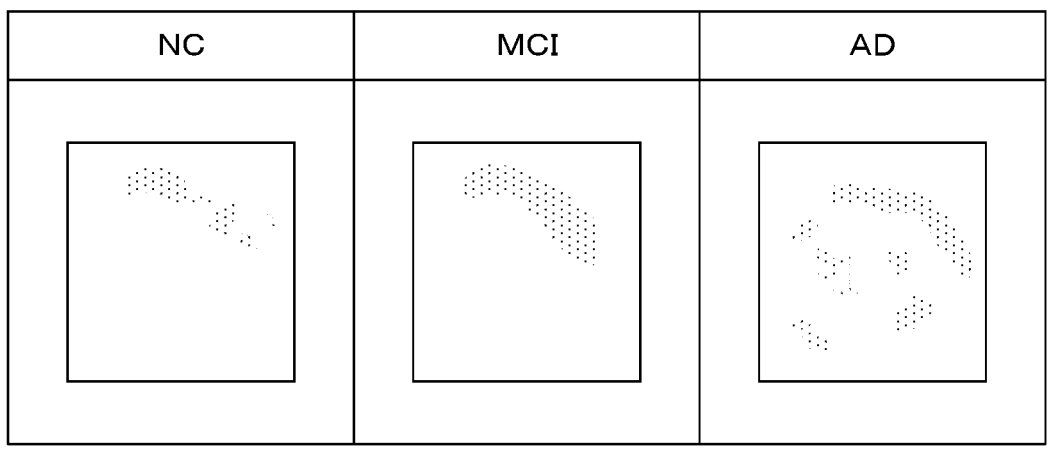
FIG. 6 is a schematic view illustrating an example of a distribution state of amyloid $\beta$ corresponding to cognitive impairment.

FIG. 6 is a schematic view illustrating an example of a distribution state of amyloid β which corresponds to cognitive impairment. FIG. 6 schematically illustrates a distribution state of amyloid β in the brain of subjects of health elderly (NC), mild cognitive impairment (MCI), and Alzheimer disease (AD). Note that, the distribution state may be different from an actual distribution state of amyloid In a case of NC, a distribution of amyloid β is hardly seen. On the other hand, in a case of AD, it can be seen that deposition of amyloid β has occurred in a plurality of portions in the brain.

In diagnosis of Alzheimer's disease, voxel based morphometry (VBM) capable of objectively evaluating the degree of brain atrophy from a three-dimensional image of MRI may be used in many cases. In the progress of the Alzheimer disease, the brain atrophy occurs at a late stage of MCI or at a stage of AD. However, the Alzheimer disease may be developed at a point of time (for example, over a decade ago) before diagnosis of the disease with an MRI image such as the T1-weighted image in many cases. That is, the T1-weighted image is not a sufficient biomarker. On the other hand, it is considered that deposition of senile plaques due to amyloid β is a pathological change that occurs from the earliest stage of a development process of Alzheimer disease, and is said to begin over 10 years before clinical symptoms appear. As illustrated in FIG. 6, in a case of MCI, it can be seen that the distribution of amyloid β is more significant in comparison to NC. As described above, according to the brain state estimation method of this embodiment, since it is possible to diagnose the development at an extremely early stage in the development progress of Alzheimer disease, the method is useful for early detection of cognitive impairment of a subject, and is also useful for research of preclinical Alzheimer disease.

FIG. 7 is a schematic view illustrating a second example of the brain state estimation result obtained by the estimation unit 55. FIG. 7 illustrates a current distribution state of amyloid β in the brain of any subject, and distribution states after one year and two years, respectively. In order to estimate the distribution state of amyloid β after one year, a time-series model that is constructed with a specific period set to one year may be used. As an example of construction of the time-series model, generation of a model (trained model) by machine learning can be performed. In addition, in order to estimate the distribution state of amyloid β after two years, a time-series model that is constructed with the specific period set to two years may be used. Specifically, the estimation unit 55 can estimate neurodegenerative diseases including dementia of a subject in the future on the basis of a correlation image that is output from the model unit 552 and represents a correlation between a magnetic susceptibility of the brain of a subject and amyloid β. In the example in FIG. 7, at the current point of time, it is possible to predict that the subject is diagnosed as MCI, but may be diagnosed as AD after two years. Note that, the example in FIG. 7 is illustrative only, and is not limited to after one year, and after two years. In addition, similarly, it is possible to estimate that a person who is currently healthy may suffer from mild cognitive impairment (MCI) in the future, or MCI is currently developed but AD may be developed in the future.

Figure 8:
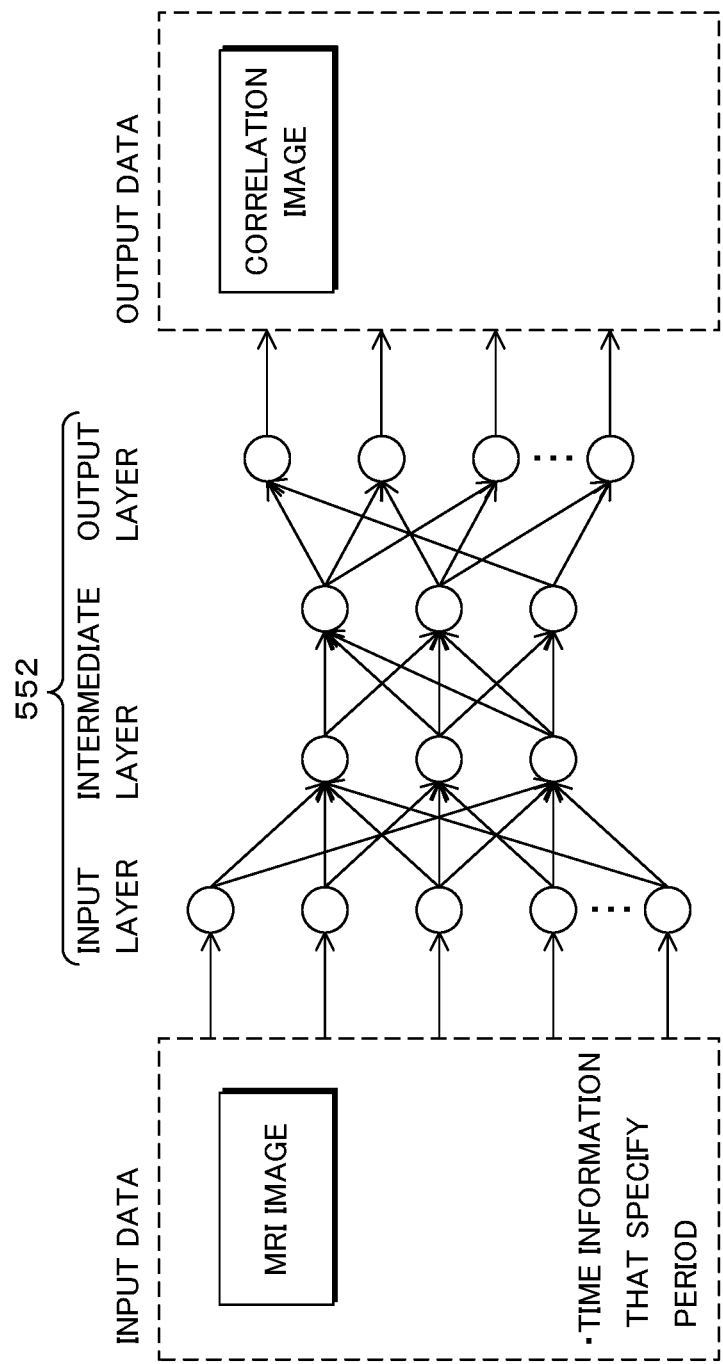
FIG. 8 is a schematic view illustrating a second example of the brain state estimation method by the estimation unit.

FIG. 8 is a schematic view illustrating a second example of the brain state estimation method by the estimation unit 55. A configuration of the model unit 552 is similar to the first example illustrated in FIG. 2. The input data generation unit 551 inputs time information that specifies a period to the model unit 552 as input data in addition to an MRI image. The period to be specified is a period (specific period) for specifying estimation of a brain state at a point of time after passage of how long period from a brain state at a certain point of time, and can be set to one year, two years, and the like.

In a case where the time information for specifying the period is input in combination with the MRI image, the model unit 552 can output a correlation image representing a correlation between a magnetic susceptibility of the brain, which is represented by the MRI image, after the period, and amyloid β. For example, in a case where the specific period is set to one year, the model unit 552 can output a correlation image representing a correlation between a magnetic susceptibility of the brain and amyloid β after one year, and in a case where the specific period is set to two years, the model unit 552 can output a correlation image representing a correlation between a magnetic susceptibility of the brain and amyloid β after two years.

As described above, in a case where time information specifying a period is input to the model unit 552, it is possible to estimate a distribution state of amyloid β in the brain of a subject after the period that is specified by the time information. In addition, in a case where time information specifying a required period is input to the model unit 552, it is possible to estimate a distribution state of amyloid β in the brain of the subject after passage of the required period from the current time only by obtaining an MRI image of a current brain state of the subject.

Figure 9:
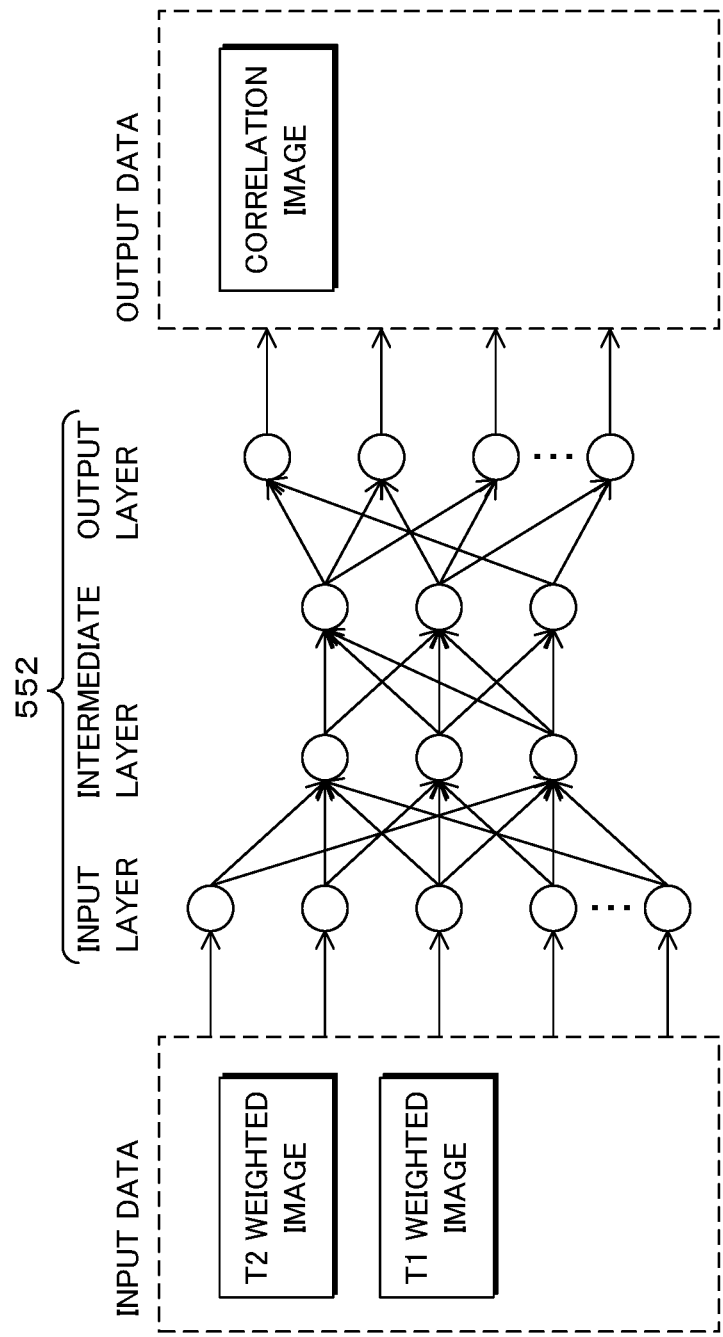
FIG. 9 is a schematic view illustrating a third example of the brain state estimation method by the estimation unit.

FIG. 9 is a schematic view illustrating a third example of the brain state estimation method by the estimation unit 55. A configuration of the model unit 552 is similar to the first example illustrated in FIG. 2. The input data generation unit 551 inputs a T1-weighted image and a T2-weighted image of the brain of a subject to the model unit 552. Note that, in the example in FIG. 9, an aspect in which the T1-weighted image and the T2-weighted image are directly input to the model unit 552 is illustrated. However, there is no limitation to the aspect, and a process of image processing to the T1-weighted image and the T2-weighted image may be provided, and images after the image processing may be input to the model unit 552.

That is, the estimation unit 55 acquires the T1-weighted image and the T2-weighted image based on the MRI image of the subject, inputs the acquired T1-weighted image and T2-weighted image to the model unit 552 that outputs a correlation image representing a correlation between a magnetic susceptibility capable of being specified on the basis of the T2-weighted image and amyloid β in a case where the T1-weighted image and the T2-weighted image are input, and can output the correlation image representing the correlation between the magnetic susceptibility of the subject and amyloid β.

The T2-weighted image can be used in detection of iron deposition. The T1-weighted image can emphasize substances other than water and blood, and for example, the thickness of cortex over the entire region from neocortex to cerebrum cortex in the brain can be observed. It is known that senile plaque due to amyloid β starts to be accumulated from a base portion of neocortex, and broadens to the entire region of cerebrum cortex. In addition, in Alzheimer's disease, it is known that an atrophy rate in each cortex such as lateral temporal lobe cortex and posterior corpus callosum ampulla cortex gradually increases.

In a case where the T1-weighted image and the T2-weighted image are input, the model unit 552 can output the correlation image representing the correlation between the magnetic susceptibility capable of being specified on the basis of the T2-weighted image and amyloid β. In this case, the model unit 552 can also estimate a current distribution state of amyloid β, but the model unit 552 can determine whether to estimate how much future distribution state (for example, after one year, after two years, or the like) of amyloid β as a specific period in advance.

Since the model unit 552 is trained by using the T1-weighted image, it is possible to estimate the future distribution state of amyloid β in the brain of the subject with more accuracy in consideration of expansion, an atrophy rate of senile plaque in the brain, or the like. According to this, it is possible to estimate the early signs of diseases relating to amyloid β such as dementia with more accuracy without using the PET image.

Note that, although not illustrated in the drawing, in the example in FIG. 9, time information as illustrated in FIG. 8 may be further input. According to this, the model 552 can estimate the distribution state of amyloid β in the brain of the subject at the point of time (in the future) after passage of the specific period specified by the input time information with more accuracy.

Next, the trained model generation method will be described.

Figure 10:
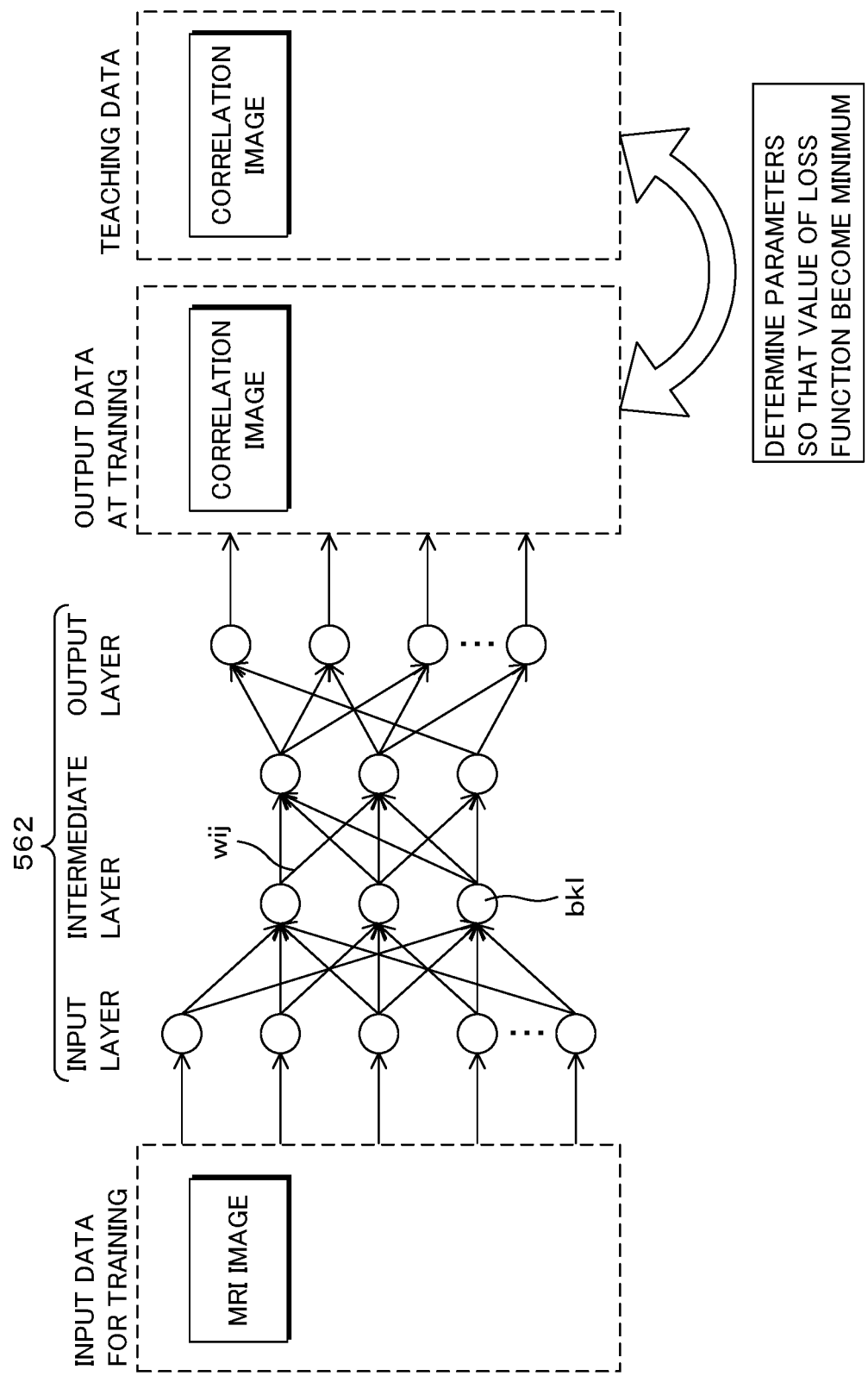
FIG. 10 is a schematic view illustrating a first example of a trained model generation method in a training processing unit.

FIG. 10 is a schematic view illustrating a first example of the trained model generation method in the training processing unit 56. For example, the model unit 562 can be constituted by a neural network. The training data generation unit 561 acquires an MRI image relating to the brain as input data for training, acquires a correlation image representing a correlation between a magnetic susceptibility and amyloid β as teaching data, and supplies the correlation image to the model unit 562. In a case where the MRI image is input to the model unit 562, the parameter determination unit 563 adjusts parameters (for example, a weight wij and a bias bkl) of the model unit so that the correlation image output from the model unit 562 approaches the correlation image as the teaching data (so that a value of a loss function becomes the minimum), and finally determines the parameters. According to this, a trained model can be generated. In this case, the correlation image output from the model unit 562, and the correlation image as the teaching data represent a correlation between a magnetic susceptibility of the brain and amyloid β after passage of a specific period (for example, one year, two years, or the like) from the point of time at which a magnetic susceptibility represented by the MRI image is obtained.

Figure 11:
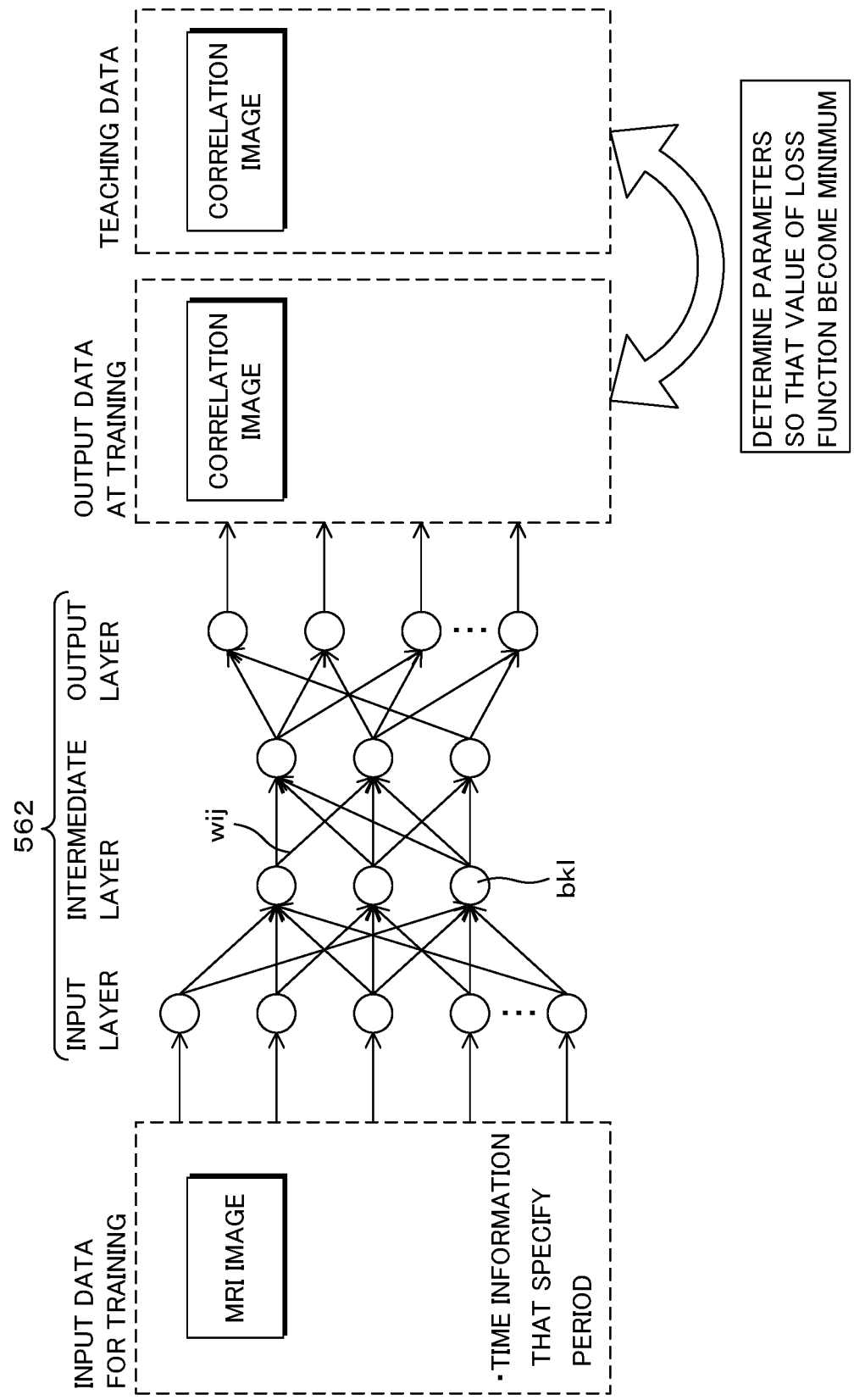
FIG. 11 is a schematic view illustrating a second example of the trained model generation method in the training processing unit.

FIG. 11 is a schematic view illustrating a second example of the trained model generation method in the training processing unit 56. The model unit 562 is similar to the first example illustrated in FIG. 10. The training data generation unit 561 acquires time information that specifies a period as input data for training in addition to the MRI image relating to the brain, acquires a correlation image representing a correlation between a magnetic susceptibility and amyloid β as teaching data, and provides the correlation image to the model unit 562. According to this, the time information that specifies the period is further input to the model unit 562, and it is possible to train that the correlation image output from the model unit 562 is a correlation image representing a correlation between a magnetic susceptibility of the brain after the period which is represented by the MRI image, and amyloid β. According to this, the model unit 552 illustrated in FIG. 8 can be generated.

Although not illustrated in the drawing, in order to generate the model unit 552 illustrated in FIG. 9, the T1-weighted image and the T2-weighted image may be input to the model unit 562 illustrated in FIG. 10. That is, the T1-weighted image and the T2-weighted image are input to the model unit 562, and parameters (for example, a weight wij and a bias bkl) of the model unit 562 are adjusted so that the correlation image output from the model unit 562 approaches the correlation image as the teaching data. According to this, a trained model can be generated. In addition, in the example in FIG. 9, in order to generate the model unit 552 capable of further inputting time information as exemplified in FIG. 8, the T1-weighted image, the T2-weighted image, and the time information may be input to the model unit 562 illustrated in FIG. 10.

Training of the model unit 562 can be performed by individually using a correlation image in each of a cluster unit that is a set of voxels, a voxel unit, and a region of interest unit. In this specification, the voxel is the smallest constituent unit of a three-dimensional image, and a small-volume cube having a scalar value or a vector value. The cluster is a three-dimensional region constituted by a plurality of voxels. The region of interest (ROI) is a specified and narrowed region for observation or measurement.

Next, an operation of the server 50 will be described.

Figure 12:
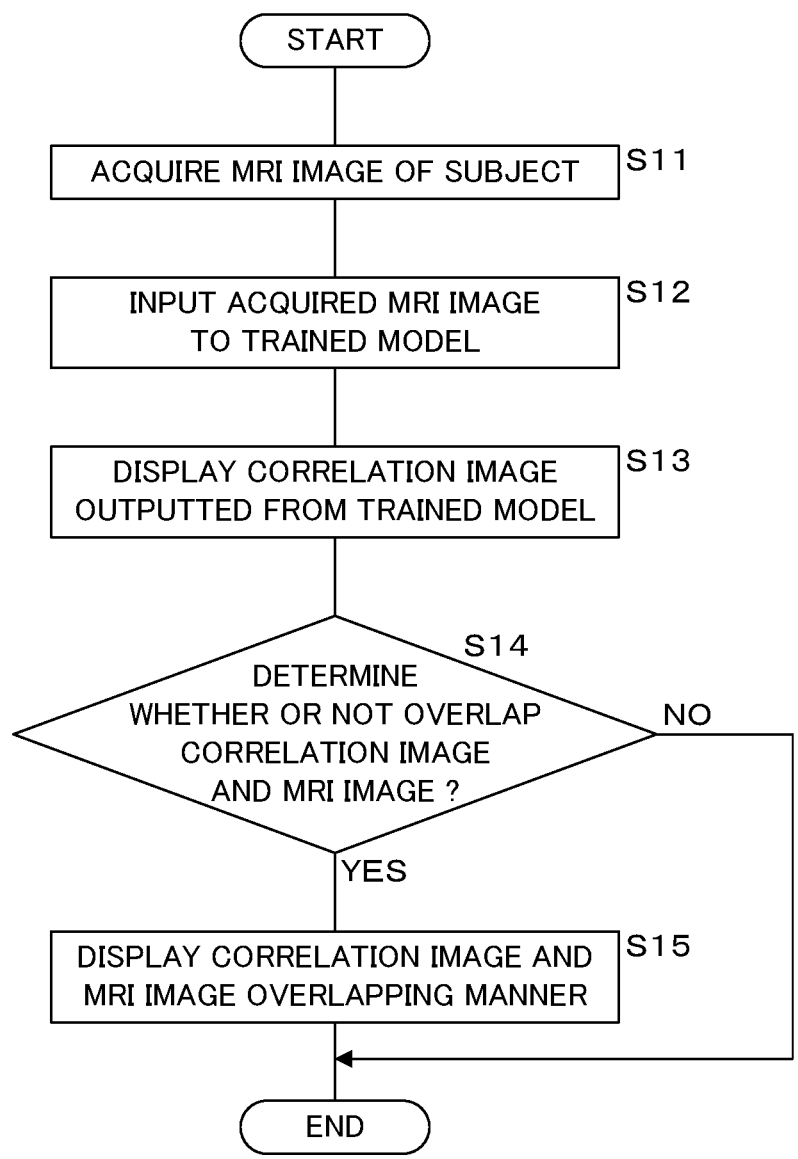
FIG. 12 is a flowchart illustrating an example of a procedure of a brain state estimation process.

FIG. 12 is a flowchart illustrating an example of a procedure of a brain state estimation process. Hereinafter, description will be given on the assumption that the control unit 51 is set as the subject of the process for convenience. The control unit 51 acquires an MRI image of a subject (S11). For example, the MRI image may be the T2-weighted image, the QSM image, a combination of the T2-weighted image and the T1-weighted image, or a combination of the QSM image and the T1-weighted image. The control unit 51 inputs the acquired MRI image to the trained model (S12).

The control unit 51 causes the terminal device 10 to display a correlation image that is output from the trained model (S13), and determines whether or not to overlap the correlation image and the MRI image (for example, the T1-weighted image) each other (S14). Note that, whether or not to overlap the correlation image and the MRI image each other can be determined on the basis of an instruction from the terminal device 10. In a case where the correlation image is not caused to overlap the MRI image (NO in S14), the control unit 51 terminates the process. In a case where the correlation image is caused to overlap the MRI image (YES in S14), and the control unit 51 causes the terminal device 10 to display the correlation image and the MRI image in an overlapping manner (S15), and terminates the process.

FIG. 13 is a flowchart illustrating an example of a procedure of a trained model generation process. The control unit 51 reads out a model (S21), and sets an initial value of a parameter of a neural network (S22). The control unit 51 acquires an MRI image (S23) and acquires a correlation image as teaching data (S24). Here, for example, the MRI image may be the T2-weighted image, the QSM image, a combination of the T2-weighted image and the T1-weighted image, or a combination of the QSM image and the T1-weighted image.

The control unit 51 input the MRI image to a model, and adjusts the parameter of the neural network so that a value of a loss function based on the correlation image output from the model and the correlation image acquired as teaching data becomes the minimum (S25).

The control unit 51 determines whether or not the value of the loss function is within an allowable range (S26), and in a case where the value of the loss function is not within the allowable range (NO in S26), the control unit 51 continues a process subsequent to step S25. In a case where the value of the loss function is within the allowable range (YES in S26), the control unit 51 stores a generated trained model (S27) and terminates the process.

As illustrated in FIG. 14, the server 50 can also be realized by using a computer provided with a CPU (processor) 501, a ROM 502, a RAM 503, recording medium reading unit 504, and the like. A computer program, recorded on a recording medium 505, that defines the procedures of the processes as illustrated in FIG. 12 and FIG. 13 is read out by a recording medium reading unit 504 provided in the computer, and the read-out computer program is loaded on the RAM 503, and the computer program is executed by the CPU (processor) 501. According to this, the server 50 can be realized on the computer.

In the above-described embodiment, description has been given of accumulation of amyloid β mainly in the brain. However, this embodiment is not limited to a portion in the brain, and in a case where accumulation of amyloid β in another portion other than the brain relates to a certain disease, this embodiment is also applicable to the portion.

A computer program of this embodiment causes a computer to execute processes of: acquiring an MRI image of a subject; and inputting the acquired MRI image to a trained model that outputs a correlation image representing a correlation between a magnetic susceptibility capable of being specified on the basis of the MRI image and amyloid β in a case where the MRI image is input, and outputting the correlation image representing the correlation between the magnetic susceptibility of the subject and amyloid β.

An information processing device of this embodiment includes: an acquisition unit that acquires an MRI image of a subject; and an output unit that inputs the acquired MRI image to a trained model that outputs a correlation image representing a correlation between a magnetic susceptibility capable of being specified on the basis of the MRI image and amyloid β in a case where the MRI image is input, and outputs the correlation image representing the correlation between the magnetic susceptibility of the subject and amyloid β.

An information processing method of this embodiment includes: acquiring an MRI image of a subject; and inputting the acquired MRI image to a trained model that outputs a correlation image representing a correlation between a magnetic susceptibility capable of being specified on the basis of the MRI image and amyloid β in a case where the MRI image is input, and outputting the correlation image representing the correlation between the magnetic susceptibility of the subject and amyloid β.

A trained model generation method of this embodiment includes: acquiring an MRI image; acquiring a correlation image representing a correlation between a magnetic susceptibility and amyloid β; and generating a trained model that outputs a correlation image representing a correlation between a magnetic susceptibility capable of being specified on the basis of the MRI image, and amyloid β by using the acquired MRI image and the correlation image.

A correlation image output device of this embodiment outputs a correlation image representing a correlation between a magnetic susceptibility of a subject and amyloid β in a case where an MRI image of the subject is input.

The computer program acquires an MRI image of a subject. The MRI image includes the T1-weighted image and the T2-weighted image. A complex image composed of a real part and an imaginary part can be generated by performing reconstruction processing to a magnetic resonance (MR) signal. An intensity image is an image representing an absolute value of a real part and an imaginary part of each pixel. A phase image representing a phase between the real part and the imaginary part of each pixel is an image representing a phase difference that occurs due to a magnetic susceptibility difference between biological tissues. Examples of the intensity image and the phase image include the T1-weighted image, the T2-weighted image, and the like. In addition, the MRI image may include an image that is generated from the MRI image by predetermined image processing. For example, a quantitative susceptibility mapping (QSM) image is also referred to as a quantitative magnetic susceptibility mapping image, and can be generated from the MRI image. The QSM image is mapped by quantitatively obtaining a local magnetic susceptibility from a phase image. The magnetic susceptibility is a physical value that represents the likelihood of magnetic polarization (magnetization) that occurs when a substance reacts with an external magnetic field, and since all substances have a weak diamagnetism, a biological tissue shows a slightly negative magnetic susceptibility, and shows a positive magnetic susceptibility when iron deposition occurs.

The trained model can output a correlation image representing a correlation between a magnetic susceptibility capable of being specified on the basis of an MRI image and amyloid β in a case where the MRI image is input. The magnetic susceptibility capable of being specified on the basis of the MRI image is a magnetic susceptibility capable of being specified, for example, on the basis of an MRI image such as the T2-weighted image and the QSM image, or an image obtained from the MRI image by image processing. That is, the MRI image can include an image that can specify the magnetic susceptibility and can be generated from the MRI image. The correlation image specifies a correlation coefficient r between a magnetic susceptibility and a PET signal (for example, standardized uptake value ratio (SUVR)) of a PET image for every corresponding pixel (voxel) of the MRI image (for example, the QSM image) and the PET image. For example, the correlation coefficient r can be set to satisfy a relationship of $0 \le r \le 1$, and as the correlation coefficient r is closer to 1, the correlation is larger.

A model before training (also simply referred to as "model") can be constituted, for example, by a neural network. An MRI image is acquired as input data for training, and a correlation image representing a correlation between a magnetic susceptibility capable of being specified on the basis of the MRI image and amyloid β is acquired as teaching data. The MRI image is input to the model, and parameters (for example, a weight and a bias) of the model are adjusted so that the correlation image output from the model approaches a correlation image as the teaching data. According to this, a trained model can be generated.

That is, the acquired MRI image of a subject is input to the trained model to estimate a distribution state of amyloid β of the subject. According to this, it is possible to estimate the early signs of diseases relating to amyloid β without using a PET image.

The computer program of this embodiment causes a computer to execute processes of: acquiring a T1-weighted image and a T2-weighted image based on the MRI image of the subject; and inputting the acquired T1-weighted image and the T2-weighted image to the trained model that outputs a correlation image representing a correlation between a magnetic susceptibility capable of being specified on the basis of the T2-weighted image and amyloid β in a case where the T1-weighted image and the T2-weighted image are input, and outputting the correlation image representing the correlation between the magnetic susceptibility of the subject and amyloid β.

The computer program acquires the T1-weighted image and the T2-weighted image based on the MRI image of the subject. The T2-weighted image can be used in detection of iron deposition. The T1-weighted image can emphasize substances other than water and blood, and for example, the thickness of cortex over the entire region from neocortex to cerebrum cortex in the brain can be observed. It is known that senile plaque due to amyloid β starts to be accumulated from a base portion of neocortex, and broadens to the entire region of cerebrum cortex. In addition, in Alzheimer's disease, it is known that an atrophy rate in each cortex such as lateral temporal lobe cortex and posterior corpus callosum ampulla cortex gradually increases.

In a case where the T1-weighted image and the T2-weighted image are input, the trained model can output the correlation image representing the correlation between the magnetic susceptibility capable of being specified on the basis of the T2-weighted image and amyloid β. The T1-weighted image and the T2-weighted image are input to the model, and parameters (for example, a weight and a bias) of the model are adjusted so that the correlation image output from the model approaches the correlation image as the teaching data. According to this, a trained model can be generated.

Since the trained model is trained by using the T1-weighted image, it is possible to estimate the distribution state of amyloid β of the subject with more accuracy in consideration of expansion or an atrophy rate of senile plaque, or the like. According to this, it is possible to estimate the early signs of diseases relating to amyloid β with more accuracy without using the PET image.

In the computer program of this embodiment, in a case where an MRI image relating to the brain is input, the trained model outputs a correlation image representing a correlation between a magnetic susceptibility of the brain after a specific period, and amyloid β.

In a case where the MRI image relating to the brain is input, the trained model outputs a correlation image representing a correlation between a magnetic susceptibility of the brain after a specific period, and amyloid β. The trained model can be generated as follows. An MRI image relating to the brain is acquired as input data for training, and a correlation image representing a correlation between a magnetic susceptibility of the brain after the specific period which is represented by the MRI image, and amyloid β is acquired as teaching data. The MRI image is input to the model, and parameters (for example, a weight and a bias) of the model are adjusted so that the correlation image output from the model approaches a correlation image as the teaching data. According to this, a trained model can be generated. In this case, the correlation image output from the model and the correlation image as the teaching data represent a correlation between a magnetic susceptibility of the brain and amyloid β after passage of a specific period (for example, one year, two years, or the like) from the point of time at which a magnetic susceptibility represented by the MRI image is obtained. According to this, when an MRI image of the brain at any point of time is obtained, it is possible to estimate a distribution state of amyloid β in the brain after passage of a specific period from the point of time.

The computer program of this embodiment causes the computer to execute processes of: acquiring time information specifying a period; and inputting the acquired time information to the trained model that outputs a correlation image representing a correlation between a magnetic susceptibility, which is capable of being specified on the basis of the MRI image, of a brain after the period, and amyloid β in a case where the time information specifying the period is input, and outputting the correlation image representing the correlation between the magnetic susceptibility of the brain of the subject after the period and amyloid β.

The computer program acquires time information that specifies a period. The period to be specified is a period for specifying estimation of a brain state at a point of time after passage of how long period from a brain state at a certain point of time.

In a case where the time information that specifies a period is further input, the trained model can output a correlation image representing a correlation between a magnetic susceptibility, which is capable of being specified on the basis of the MRI image, of the brain after the period, and amyloid β. The time information that specifies the period is further input to the model, and it is possible to train that the correlation image output from the model is a correlation image representing a correlation between a magnetic susceptibility, which is capable of being specified on the basis of the MRI image, of the brain after the period, and amyloid β.

In a case where time information specifying a period is input to the trained model, it is possible to estimate a distribution state of amyloid β in the brain of a subject after the period that is specified by the time information. In addition, in a case where the time information is set as time information that specifies a required period, for example, it is possible to estimate a distribution state of amyloid β in the brain of the subject after passage of the required period from the current time only by obtaining an MRI image of a current brain state of the subject.

The computer program of this embodiment causes the computer to execute a process of estimating a neurodegenerative disease including dementia of the subject in the future on the basis of the trained model's output of the correlation image that represents the correlation between the magnetic susceptibility of the brain of the subject and amyloid β.

The computer program can estimate a neurodegenerative disease including dementia of the subject in the future on the basis of the trained model's output of the correlation image that represents the correlation between the magnetic susceptibility of the brain of the subject and amyloid β. For example, it is possible to estimate whether or not a disease such as dementia relating to accumulation of amyloid β is developed in a subject in accordance with the magnitude of a variation rate of accumulation (degree of accumulation) of amyloid β.

In the computer program of this embodiment, the correlation image represents a correlation between a magnetic susceptibility in a cluster unit that is a set of voxels, in a voxel unit, or in a region of interest unit, and amyloid β.

The correlation image can represent the correlation between the magnetic susceptibility in each of the cluster unit that is a set of voxels, the voxel unit, and the region of interest unit, and amyloid β. The voxel is the smallest constituent unit of a three-dimensional image, and a small-volume cube having a scalar value or a vector value. The cluster is a three-dimensional region constituted by a plurality of voxels. The region of interest (ROI) is a specified and narrowed region for observation or measurement. Training of the model can be performed by individually using a correlation image in each of the cluster unit that is a set of voxels, the voxel unit, and the region of interest unit.

The computer program of this embodiment causes the computer to execute a process of displaying the correlation image output from the trained model and another MRI image in an overlapping manner.

The computer program can display the correlation image output from the trained model and another MRI image in an overlapping manner. As the other MRI image, for example, the T1-weighted image having a characteristic in which a structure of the brain is easy to see can be used. According to this, it is possible to easily determine that the distribution state of amyloid β which is represented by the correlation image corresponds to which portion of the brain.

It is to be noted that, as used herein and in the appended claims, the singular forms "a", "an", and "the" include plural referents unless the context clearly dictates otherwise.

As this invention may be embodied in several forms without departing from the spirit of essential characteristics thereof, the present embodiments are therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. A computer readable non-transitory recording medium recording a computer program causing a computer to execute processes of:
   acquiring an MRI image of a subject; and
   inputting the acquired MRI image to a trained model, the trained model composed of a neural network including an input layer, an intermediate layer, and an output layer outputs a correlation image from the output layer and generated by machine learning, that, which is an image in which the correlation coefficient is specified for a cluster unit that is set of voxels, a voxel unit, or a region of interest unit between a magnetic susceptibility capable of being specified on the basis of the MRI image and amyloid β estimated without PET imaging in a case where the MRI image is input to the input layer, and outputting the correlation image, which is an image in which the correlation coefficient is specified for a cluster unit that is set of voxels, a voxel unit, or a region of interest unit between the magnetic susceptibility of the subject and amyloid β estimated without PET imaging.

2. The computer readable non-transitory recording medium recording the computer program according to claim 1, further causing the computer to execute processes of:
   acquiring a T1-weighted image and a T2-weighted image based on the MRI image of the subject; and
   inputting the acquired T1-weighted image and the T2-weighted image to the trained model that outputs a correlation image representing a correlation between a magnetic susceptibility capable of being specified on the basis of the T2-weighted image and amyloid β in a case where the T1-weighted image and the T2-weighted image are input, and outputting the correlation image representing the correlation between the magnetic susceptibility of the subject and amyloid β.

3. The computer readable non-transitory recording medium recording the computer program according to claim 1,
   wherein in a case where an MRI image relating to a brain is input, the trained model outputs a correlation image representing a correlation between a magnetic susceptibility of the brain after a specific period, and amyloid β.

4. The computer readable non-transitory recording medium recording the computer program according to claim 1, further causing the computer to execute processes of:
   acquiring time information specifying a period; and
   inputting the acquired time information to the trained model that outputs a correlation image representing a correlation between a magnetic susceptibility, which is capable of being specified on the basis of the MRI image, of a brain after the period, and amyloid β in a case where the time information specifying the period is further input, and outputting the correlation image representing the correlation between the magnetic susceptibility of the brain of the subject after the period and amyloid β.

5. The computer readable non-transitory recording medium recording the computer program according to claim 1, further causing the computer to execute a process of:
   estimating a neurodegenerative disease including dementia of the subject in the future on the basis of the trained model's output of the correlation image that represents the correlation between the magnetic susceptibility of the brain of the subject and amyloid β.

6. The computer readable non-transitory recording medium recording the computer program according to claim 1, further causing the computer to execute a process of:
   displaying the correlation image output from the trained model and another MRI image in an overlapping manner.

7. An information processing device, comprising:
   an acquisition unit that acquires an MRI image of a subject; and
   an output unit that inputs the acquired MRI image to a trained model, the trained model composed of a neural network including an input layer, an intermediate layer, and an output layer and generated by machine learning, that outputs a correlation image from the output layer, which is an image in which the correlation coefficient is specified for a cluster unit that is set of voxels, a voxel unit, or a region of interest unit between a magnetic susceptibility capable of being specified on the basis of the MRI image and amyloid β estimated without PET imaging in a case where the MRI image is input to the input layer, and outputs the correlation image, which is an image in which the correlation coefficient is specified for a cluster unit that is set of voxels, a voxel unit, or a region of interest unit between the magnetic susceptibility of the subject and amyloid β estimated without PET imaging.

8. An information processing method, comprising:
   acquiring an MRI image of a subject; and inputting the acquired MRI image to a trained model, the trained model composed of a neural network including an input layer, an intermediate layer, and an output layer and generated by machine learning, that outputs a correlation image from the output layer, which is an image in which the correlation coefficient is specified for a cluster unit that is set of voxels, a voxel unit, or a region of interest unit between a magnetic susceptibility capable of being specified on the basis of the MRI image and amyloid β estimated without PET imaging in a case where the MRI image is input to the input layer, and outputting the correlation image, which is an image in which the correlation coefficient is specified for a cluster unit that is set of voxels, a voxel unit, or a region of interest unit between the magnetic susceptibility of the subject and amyloid β estimated without PET imaging.

9. A trained model generation method, comprising:

acquiring an MRI image;

acquiring a correlation image, which is an image in which the correlation coefficient is specified for a cluster unit that is set of voxels, a voxel unit, or a region of interest unit between a magnetic susceptibility and amyloid β; and generating a trained model composed of a neural network including an input layer, an intermediate layer, and an output layer that outputs a correlation image from the output layer, which is an image in which the correlation coefficient is specified for a cluster unit that is set of voxels, a voxel unit, or a region of interest unit between a magnetic susceptibility capable of being specified on the basis of the MRI image inputted to the input layer, and amyloid β estimated without PET imaging by machine learning using the acquired MRI image and the correlation image.

10. A correlation image output device that outputs a correlation image, which is an image in which the correlation coefficient is specified for a cluster unit that is set of voxels, a voxel unit, or a region of interest unit between a magnetic susceptibility of a subject and amyloid β estimated without PET imaging in a case where an MRI image of the subject is input.

* * * * *